United States Patent [19]

Lee

[11] 4,209,909
[45] Jul. 1, 1980

[54] DENTAL APPARATUS

[76] Inventor: Robert L. Lee, 22937 Grand Terrace, Colton, Calif. 92324

[21] Appl. No.: 814,815

[22] Filed: Jul. 11, 1977

Related U.S. Application Data

[63] Continuation-in-part of Ser. No. 581,208, May 27, 1975, Pat. No. 4,034,475, which is a continuation-in-part of Ser. No. 485,158, Jul. 1, 1974, Pat. No. 4,034,474.

[51] Int. Cl.² ............................................. A61C 11/00
[52] U.S. Cl. ........................................................ 433/57
[58] Field of Search ................................. 32/32, 20, 21

[56] References Cited

U.S. PATENT DOCUMENTS

| | | | |
|---|---|---|---|
| 2,816,360 | 12/1957 | Stuart | 32/32 |
| 3,224,096 | 12/1965 | Stuart | 32/32 |
| 3,478,431 | 11/1969 | DePietro | 32/32 |
| 3,590,487 | 7/1971 | Guichet | 32/32 |
| 3,694,919 | 10/1972 | Lee et al. | 32/32 |
| 3,896,550 | 7/1975 | Lee | 32/32 |
| 3,897,632 | 8/1975 | Beu | 32/32 |
| 4,024,640 | 5/1977 | Guichet | 32/32 |

Primary Examiner—Louis G. Mancene
Assistant Examiner—John J. Wilson
Attorney, Agent, or Firm—Knobbe, Martens, Olson, Hubbard & Bear

[57] ABSTRACT

Styluses defining a hinge axis in a dental articulator are received in guide block pathways defined by side walls and a curved upper wall. The blocks are rotatably mounted to vary the slope of the upper wall. A supply of guide blocks is provided having a medial wall with a rear curved portion which varies for different blocks based on average values. The user selects the blocks having the desired medial wall to provide the desired side shift. In one arrangement, the side walls are formed as a unit and removeably mounted on the upper wall and the user selects the side wall unit from a supply of units providing different degrees of side shift movement. In another form, the medial wall is transversely adjustable.

4 Claims, 14 Drawing Figures

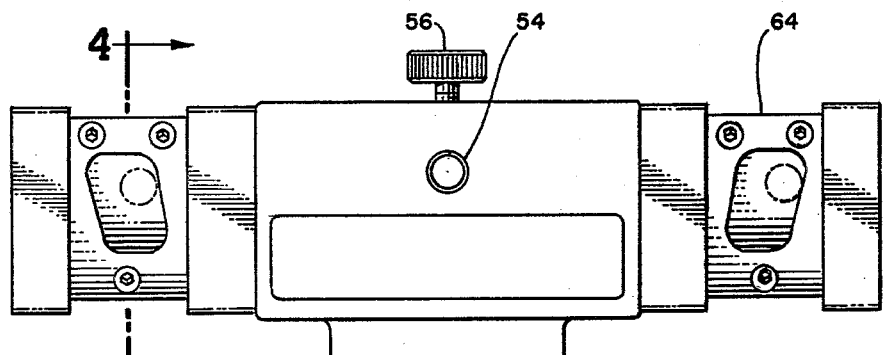
FIG. 3.
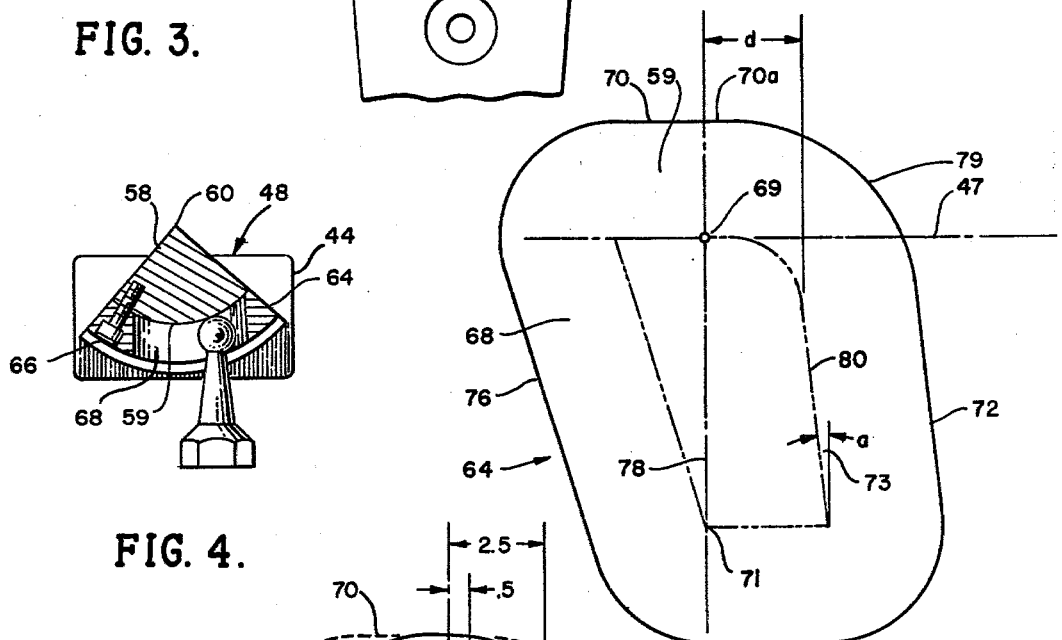
FIG. 4.
FIG. 5.
FIG. 6.

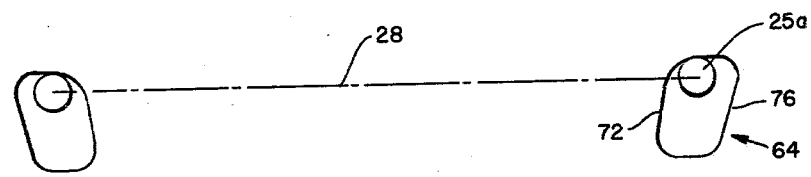
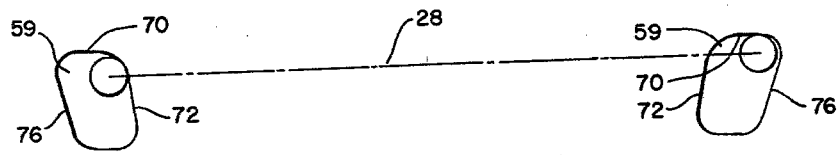
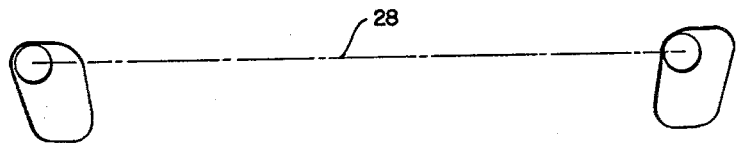
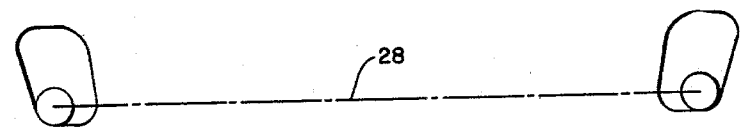
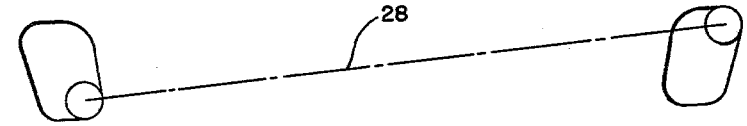
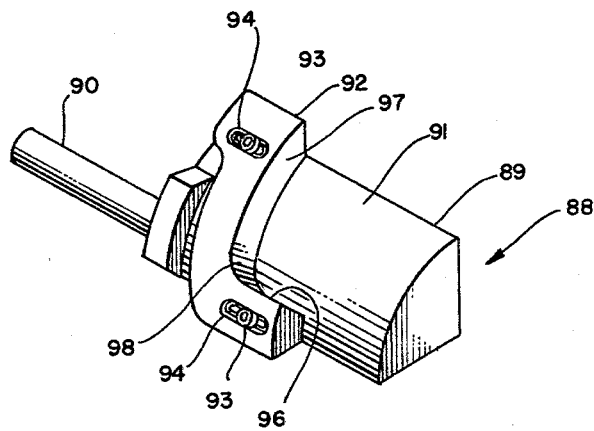
FIG. 8.

DENTAL APPARATUS

CROSS REFERENCE TO RELATED APPLICATIONS

This application is a continuation-in-part of U.S. patent application, Ser. No. 581,203, filed May 27, 1975, now U.S. Pat. No. 4,034,475 dated July 12, 1977 which in turn is a continuation-in-part of U.S. patent application No. 485,158, filed July 1, 1974, now U.S. Pat. No. 4,034,474 dated July 12, 1977.

This invention relates to dental apparatus and more particularly to an improved system for simulating jaw movement.

In U.S. Pat. No. 3,452,439-Lee, there is described a system of jaw movement simulation wherein dynamic movements of the patient's jaws are recorded, and from this information plastic blocks are formed having three-dimensional openings or pathways cut therein that may be used with a dental articulator to simulate or almost duplicate particular jaw movement. The apparatus and method employed is very precise and provides excellent results. However, the apparatus and method of operating it is relatively expensive such that the equipment is most practical for specialists, university research centers and other such large facilities.

In the above-referenced copending U.S. patent applications, there is disclosed a simplified system for measuring jaw movements, with such information being useful in setting and operating dental articulators. It is further suggested in those patents that plastic guide blocks of the type disclosed in the earlier Lee patent be classified according to certain characteristics of jaw movements to provide a series of average value blocks from which the pair most closely fitting the measurements of a particular patient's jaw movements may be selected. Such guide blocks have fixed curved walls which produce movement that closely simulates a patient's movement.

In U.S. Pat. No. 4,034,475 it is suggested that such guide blocks be mounted so that they can be rotated about the hinge axis, thus varying the slope of the superior or upper wall of the opening in the guide block. This further reduces the number of average value guide blocks needed in that variations of the slope of the superior wall are obtained by rotation rather than by selecting different blocks. It was also discovered through measuring and analysing a large number of patients that the angle of the medial or inner guide wall does not vary much between patients. However, people have considerable variance in immediate condylar side shift, which is the first portion of the side shift from centric relation position. This immediate side shift portion is not purely horizontal but has some protrusive and vertical components. Thus, it was found that having the guide block rotatable and having a few different categories of immediate side shift provides the capability to simulate the jaw movement of the vast majority of patients with reasonable accuracy. That is, the dentist needs only select a pair of blocks having side shift which corresponds to the jaw measurements for that patient and then rotate the blocks about the hinge axis to provide the desired superior wall slope.

A further improvement has now been discovered wherein only a single set of guide blocks is employed but the medial wall of each guide block is either adjustable or replaceable to provide a range of average value medial wall positions that will provide a range of side shift movement. The portions of the medial side wall adjacent the rear wall is curved, as is the superior wall of the guide block, so that smooth movement is obtained comparable to that obtained with the system disclosed in the above-mentioned Lee U.S. Pat. No. 3,452,439. By having the guide block rotatably mounted, the orientation of the superior wall may be easily adjusted to the desired angle.

While a curved superior wall, a curved medial wall and a rear wall will provide the necessary guidance for satisfactory jaw simulation in many operations, it is preferable that a lateral wall and a forward wall also be provided so that each stylus on the other frame of the articulator is confined within a five-walled guide block. The lateral walls are also preferably replaceably mounted on the guide blocks to provide a range of average values. In one convenient form of the invention, the rear medial, forward and lateral side walls are formed in a closed side wall loop as a separate unit that is removably mounted on the curved superior wall of the guide block. With this arrangement, the side wall unit may be easily replaced by a different unit so that a set or series of average value units may be employed. For example, a set of such units providing a range of five or six side shift measurements may be provided. Such a set of average value units will give a reasonably priced system that will provide sufficiently accurate jaw movement simulation to be practical for the average dentist. The units may be classified directly on the basis of the horizontal side shift or indirectly on the basis of change in the curvature of the beginning curved portion of the medial wall.

In another form of the invention an average value medial wall is selected and mounted on a guide block to be transversely adjusted, which thereby varies side shift.

It has further been found adequate for other than the critical curved side wall portion at the rear of the medial wall that straight side wall sections can be employed in the areas guiding the stylus, even though actual movements may not be completely straight in those areas. This provides considerable manufacturing convenience. It has also been found that the curved upper wall is sufficiently precise for the vast majority of people if the curved surface is a portion of a cylindrical surface.

For a more thorough understanding of the invention, reference may be had to the following detailed description and drawings in which:

FIG. 3 is a partial view of the articulator showing both guide blocks of the invention in a plan view;

FIG. 4 is a cross-sectional view on line 4—4 of FIG. 3 showing the curvature of the superior wall of the block;

FIG. 5 is an enlarged schematic view of one of the guide block openings;

FIG. 6 shows a guide block opening which permits a small amount of side shift superimposed on another guide block opening which provides a larger amount of side shift;

FIGS. 7A-7E show a series of views illustrating different positions of the articulator styluses within a set of guide blocks;

FIG. 8 is a perspective view of an alternate form of the invention wherein a medial wall is mounted to be transversely adjusted;

Figure 1:
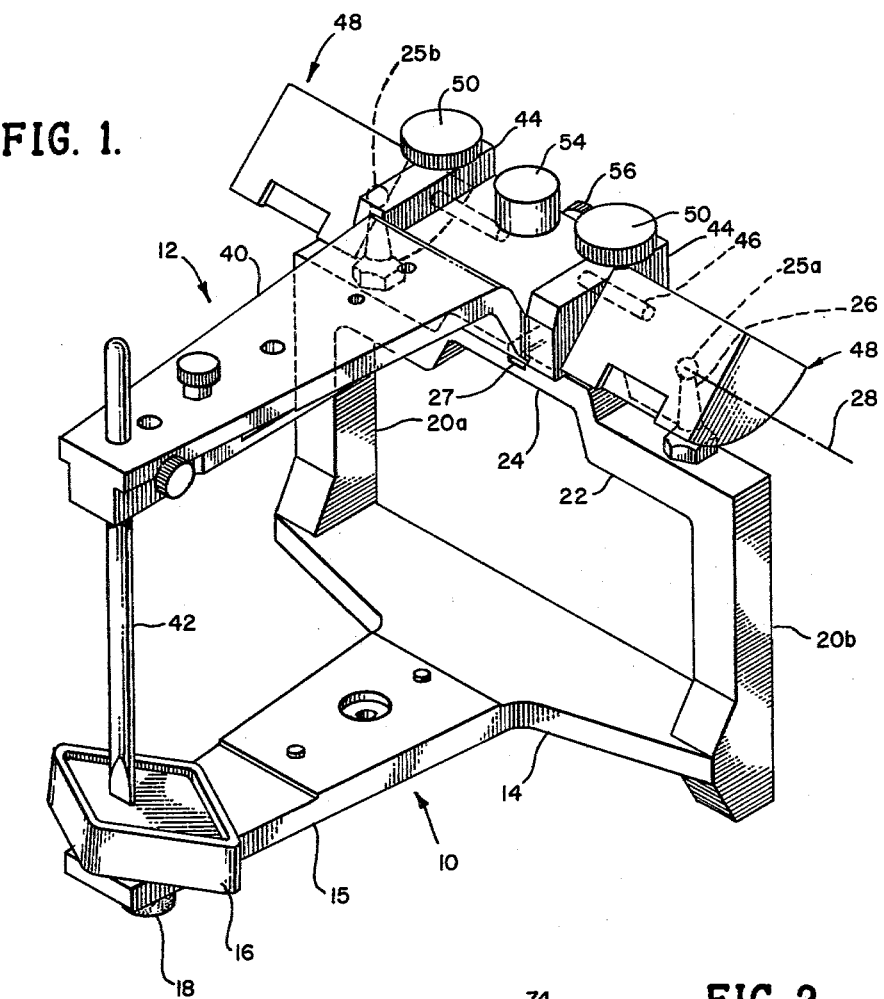
FIG. 1 is a perspective view of a dental articulator utilizing the guide blocks of the invention.
Figure 2:
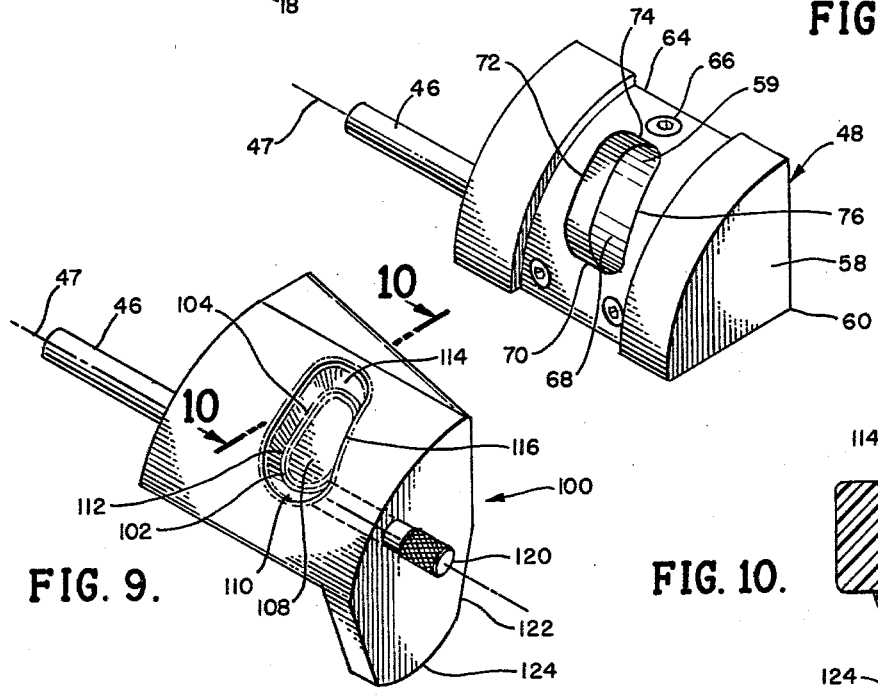
FIG. 2 is a perspective view of one of the guide blocks showing the guide opening.

Referring to FIGS. 1 and 2, there is shown a dental articulator having a lower frame or assembly 10 and an upper frame or assembly 12 which represent the lower and upper jaws of a human. In the position illustrated, the upper assembly 12 can be pivoted on the lower assembly 12 which is reversed to the human mandible or lower jaw, which slides with respect to the maxilla or upper jaw; however, the relative motion between the two frames is the same.

The lower assembly 10 includes a generally T-shaped base member 14 having a forward arm 15 supporting an incisal pin rest pad 16 on its forward end. A screw 18 extends through the arm 15 to secure the pad 16 to the base 14 and to also serve as one of three legs for the base. Formed integral with the rear of the base member 14 is a closed loop vertical frame member 20 having two posts 20a and 20b joined by a lateral truss 22. This truss has a raised center portion or bridge 24 having a centric position slot 27.

A pair of spherical styluses 25a and 25b are supported on vertical arms 26. These styluses are supported a fixed distance apart and the centers of the styluses define an axis 28 which simulates a horizontal or hinge axis of human jaw movement.

The upper assembly 12 of the articulator includes an upper frame member 40 including a forward portion which overlys the arm 15 of the lower frame member. An incisal rest pin 42 extends vertically through the forward end of the member 40 and its lower end is positioned within the pad 16. The rearward portion of the member 40 includes vertically extending support surfaces 44 on each side, each having a transversely extending opening in which is positioned a mounting pin 46 of a guide block 48. The guide blocks are rotatably mounted about their pins 46, and they may be held in a particular angular orientation by set screws 50.

A centric pin 54 extends through the central part of the upper member 40 to be received within the slot 27 in the bridge 24 of the lower member. This centric pin is used to center laterally the upper frame on the lower frame. The pin is retractable to permit lateral or side movement of the upper frame with respect to the lower frame, and the pin may be held in either upper or lower position by a set screw 56.

Referring now to FIG. 2 as well as FIGS. 1 and 3, it may be seen that each guide block 48 includes a main body member 58 in which the mounting pin 46 is fixed. The central portion of the surface 59 of the main body member which faces downwardly as viewed in FIG. 4, or upwardly as viewed in FIG. 2, is curved, preferably on a circular axis approximately around the line 60 of the body member. Positioned on the curved surface 59 of the body member 48 is a guide wall unit 64 having a curved surface which mates with the curved surface 59 of the main body member 48. This guide wall unit 64 is fixed to the main body member by three threaded fasteners 66, or other suitable means.

Within the guide wall unit, there is formed a guide pathway or opening 68 for receiving a stylus 25 of the lower frame member of the articulator. The axis 47 of the mounting pin 46 for the guide block extends through the rear portion of the opening 68 in the side wall unit. This may be more easily seen in the enlarged, schematic view of the opening 68, shown in FIG. 5, which is oriented as is the left guide block, as viewed in FIG. 3. The pin axis 47 is coincident with the stylus axis 28 through the center of the styluses 25, when the upper frame is centrally positioned on the lower frame with the styluses engaging the rear wall 70 of the guide opening. This position is identified by the point 69 and is known in the art as the centric position or the centric relation position. This position which simulates the fully retruded or rearward most position of a person's lower jaw is schematically shown in FIG. 7A. In FIGS. 1, 3 and 4, the styluses are in the guide blocks in a forward and side shifted position from centric.

The opening 68 within the side wall guide unit 64 further includes a medial wall 72, a forward wall 74, and a lateral wall 76. The rear wall 70 has a generally straight central portion which smoothly blends into the rear corner portion 79 of the medial wall 72 which then extends forwardly fairly straight but at a shallow angle with respect to a line perpendicular to the rear wall 70 or the pin axis 47 of the guide block. This is shown for purposes of illustration by the angle "a" formed by a line 73 perpendicular to the pin axis 47 and the straight portion of the broken line 80 which is parallel to the straight portion of the medial wall 72. The broken line 80 is the path of the center of a stylus as it is moved along the side walls of the guide unit 64. The line 73 is also parallel to the line 78 which represents the protrusive path of a stylus in a guide block pathway.

The forward corner of the medial wall 72 curves smoothly towards the protrusive path 78 into the short, relatively straight, forward wall 74. The forward wall in turn curves smoothly into the lateral wall 76 which has a relatively straight section and then curves smoothly into the rear wall 70. The curves at the corners are preferably on a circular radius with the radius of curvature being approximately the same for each of the corners except the corner 79 of the medial wall 72 joining the rear wall 70. The curve 79 has a radius somewhat larger than the radius for the other corners, and varies with guide pathways of different sizes.

OPERATION

In utilizing the teaching of the invention a dentist will normally employ a set of guide wall units varying in the degree of immediate side shift that they will permit. Based on measurements of the patient's jaw movements the dentist will select the pair of guide wall units to best simulate the patient's jaw movements. The immediate side shift may be defined as that distance one stylus moves medially from centric position against the curved rear portion of the medial wall 72 to the point where the curved wall portion 79 joins the straight portion of the medial wall. During this movement, the stylus is also engaging the curved upper wall 59. Accordingly, it can be seen that the immediate side shift includes not only a side movement but also includes a protrusive or forward component, and a vertical component on the curved upper wall. A measure of this immediate side shift may be most conveniently expressed by simply referring to the one dimensional, medial or horizontal movement. Thus, referring to FIG. 5, the path of the center of the stylus during the side shift movement is indicated by the broken line 80 as it moves from the centric point 69 toward the medial wall 72 to the point where the rear curved portion of the broken line 80 joins the straight portion. The horizontal distance d illustrated in FIG. 5 is a measure of the immediate side shift.

It should be recognized that the distance d is the sum of a first short straight portion 70a of the rear wall 70 plus the horizontal component of the curved rear portion of the medial portion of the path 80. Since the curve is about a circular radius, it can also be said that the distance d is equal to the straight wall portion 70a of the rear wall 70 plus the radius of the curved path of the center of the stylus as it is moved along the curved portion 79 of the medial wall. It has been found that the straight line portion 70a of the rear wall is approximately one-fourth of the distance d, with the radius of the curve providing the other three-fourths.

While the number of different side shift measurements to be provided in a set of guide wall units is a matter of choice, it is preferred that the sizes available vary in approximately one-half millimeter increments from 0 side shift to 2.5 millimeter side shift. The difference between 0.5 millimeter side shift and 2.5 millimeter side shift is illustrated in FIG. 6 wherein a schematic view of the opening 68 in a guide unit 64 having 0.5 millimeter side shift is superimposed on a unit having 2.5 millimeter side shift with the centric points 69 and the protrusive lines 78 coincident. The unit with the 2.5 millimeter side shift is numbered the same as the unit in FIG. 5, while the unit with the 0.5 millimeter side shift is identified with the same numbers but with a prime indication for convenience of comparison.

The side shift measurements 0.5 millimeter and 2.5 millimeters are marked directly on the diagram as a sidewise distance from the overlying centric position. As indicated above, the interrupted line 80 represents the center point of a stylus 25 as the articulator upper and lower members are moved through their border paths with the stylus engaging the walls of the side wall guide unit having the larger side shift. By contrast, the broken line 80' represents the border path in the unit providing the smaller side shift. As can be seen, when the stylus moves from centric position towards the medial wall 72, it moves along the curved portion 79 of the wall on a radius which is considerably larger than the radius of the curve 79' for the half millimeter side shift unit. However, beyond the curved portion, the central portions of the medial wall 72 and 72' are straight and parallel to each other, both extending at the same angle "a" of approximately six to seven degrees with respect to the protrusive path 78 perpendicular to the pin axis 47.

As mentioned above, the radius of curvature of the other three corners of the guide unit are identical, and they are the same for the various units providing varying side shift. Thus, with the arrangement illustrated, the increase in side shift between the two units near the forward wall 74 is indicated by the forward portion of the medial wall 72 being shifted to the right as viewed in FIG. 6 from the forward portion of the medial wall 72'. The full protrusive movement point 71 remains coincident with the two guide units, and the left corner adjacent the forward wall 74 is essentially coincident for the two units. However, from that area rearward, the lateral wall 76 for the larger unit diverges laterally, or to the left as viewed in FIG. 6, to accommodate the increase in side shift illustrated near the rear wall 70.

Many patients cannot actually move their mandible in a path that would correspond to movement along the lateral wall 76; but instead move the mandible rearwardly in more of a straight protrusive movement, and then move laterally. However, the dentist will frequently move the patient's mandible in the path corresponding to that along the lateral wall 76.

Referring to FIG. 7, the various positions of a pair of styluses of one frame of the articulator are illustrated as they are moved within a pair of guide units having the 2.5 millimeter side shift. As mentioned above, FIG. 7A shows the styluses in the centric position wherein both styluses engage the rear wall 70 and the upper frame of the articulator is transversely centered on the lower frame. This corresponds to the position of human jaws wherein the lower jaw in its full rearward or retruded position, and with the lower jaw laterally centered with respect to the upper.

FIG. 7b illustrates the immediate side-shift in one direction. This side-shift movement is guided by the stylus on the left moving along the rear wall towards the medial wall 72 and following the curved contour of the rear portion 79 of the medial wall. The horizontal component of this movement is represented on the drawing as the immediate side shift. During this side shift movement, the stylus on the right in FIG. 7b moves generally laterally along the rear wall 70 almost completely into the outer corner of the guide block. A slight space between the stylus on the right and the lateral wall 76 is shown in exaggerated form in the drawing to emphasize that it is the stylus on the left moving against the lateral wall 72 of the guide block on the left which guides the side shift movement.

FIG. 7C illustrates the immediate side-shift of the styluses in the opposite direction. That is, the stylus on the right moves from centric position against its medial wall both horizontally and slightly protrusively, while the stylus on the left moves generally laterally engaging the rear wall 70.

FIG. 7D illustrates the styluses in the protrusive position. Note that the styluses are located in the corner between the forward wall and the lateral wall and no side shift is permitted while in protrusive position.

FIG. 7E shows the position of the styluses wherein the left stylus as viewed in the drawing is in a forward or protrusive position, but it is shifted transversely engaging the forward portion of the medial wall. The right stylus as viewed in the drawing engages the rear wall of the guide block and is shifted laterally from centric. The position of the styluses is again guided by the left stylus engaging its adjacent medial wall, due to the angle of this medial wall. The right stylus is shifted laterally a slight amount greater than the right stylus as viewed in FIG. 7B. This position of the styluses simulates a twisting movement of the lower jaw. The reverse position is not shown but can be readily visualized.

It should be appreciated that in all of the movements of the articulator frames, the spherical surface of each of the styluses is moving on the curved surface of the main body member of the guide block 48 which forms the upper wall of the pathway in which the stylus is positioned. This curved surface coupled with the curved portion of the medial wall 72 provides movement which is much more accurate and smooth than with simply straight wall articulators. Consequently, the movement is close to that of the individualized or custom made blocks referred to in the above-identified Lee U.S. Pat. No. 3,452,439, but the system is much less costly.

If different side wall units are desired, it is only necessary to loosen the threaded fasteners and replace the unit with the desired one. In use, the operator of the instrument has a supply of the guide units classified on the basis of side shift. The desired unit is selected based on measurements of the patient's jaw movements.

It should be kept in mind that the purpose of the articulator guide blocks in combination with the spherical styluses is to simulate human jaw movement. The physical structure of the temporomandibular joint is considerably different from the guide block and stylus employed in the articulator. However, the movement provided by the articulator is similar to that provided by the human jaw. Likewise, it should be kept in mind that the wall surfaces employed in the articulator guide blocks are average values to provide average values of jaw movements. For example, the upper wall 59 of the articulator guide block is described to be on a circular radius which will provide a given movement. In actuality, this type of movement is not always on a fixed radius and the size of the radius will vary from person to person. Nevertheless, it has been found that a circular radius of an average value will provide movements corresponding to the vast majority of people. Also, the circular radius provides manufacturing convenience in fabricating the guide blocks.

Similarly, the configuration of the medial wall is selected to provide average value movements. The rear curved portion of the medial wall is said to be on a fixed radius, which thus provides a circular sector. Again, the movement in this area is not always on a circular radius for each patient but it rather surprisingly produces jaw movements that represent a large majority of the people and again there are clear manufacturing conveniences. Also, the straight portion of the medial wall of course provides straight movement, whereas in actuality, a person's movement in this area is on a curved path with a radius approximately equal to the condylar distance of the person since this distance is quite large relative to the small amount of protrusive movement occuring, the path is essentially straight.

Also, the portion of the rear wall of the guide block leading from centric position to the lateral wall is selected to provide average value movement. For many people, the rear wall actually curves slightly in this area, but a straight portion provides very satisfactory results and facilitates use of the articulator in centric position operations.

While the guide units 64 having four walls are the most desirable arrangements, it should be appreciated that the medial wall 72 together with the rear wall 70 and the upper wall 59 are the most critical in that they can determine the immediate side shift even if there is no lateral wall. That is, referring to FIGS. 7B and 7C, it can be seen that if the guide units shown did not have lateral walls 76, the medial walls 72, rear walls 70, and the top walls 59 would nevertheless determine the positioning of the styluses. Similarly, in the position such as that shown in 7E, the medial and upper walls of the unit on the left and the rear and upper walls of the right unit position the styluses. Also, it is the curvature of the medial wall which is the portion which changes from unit to unit and this portion would be retained in a three wall guide box having only a rear wall, a medial wall and an upper wall. The curved portion of the medial wall is directly proportional to the immediate side shift. Because of this, a supply of units can be classified on the basis of the radius of curvatures of the initial portion 77 of the medial wall 72.

Although it is the curved wall 79 adjoining the rear wall 50 and the medial wall 72 of a guide block which varies as the immediate side shift varies from person to person, a useful guide block is still obtained with an average value curvature for the portion 79. In FIG. 8, there is schematically illustrated a guide block 88 having a main body portion 89 which has a mounting pin 90 like the guide block in FIG. 2 and has a curved upper surface 91 identical to the curved surface 59 shown in FIG. 2. A side wall guide unit 92 is adjustably mounted on the main body member 89 by suitable threaded fastner means 93 extending through transversely extending slots 94 in the guide unit 92. The guide unit 92 forms a rear wall 96 and a medial wall 97 joined by a smoothly curved corner 98. The curvature of the corner is based on an average value which will provide movement in that area which will simulate a large percentage of the population.

With the arrangement illustrated in FIG. 8, the guide unit 92 is transversely adjustable to provide a desired range of side shift. This approach provides a very simple and useful adjustable guide block that includes the important side shift feature and provides the necessary control for the border paths in simulating jaw movement. Also, while such movements are not as accurate as that provided by the closed side wall units, the surfaces along which the styluses move are curved in three dimensions so that the movements obtained compare favorably with the custom made guide blocks and with the actual patient jaw movement.

While the rear wall 96 is part of the adjustable side wall unit, the rear wall could be fixed and only the medial wall adjusted.

Figures 9, 10:
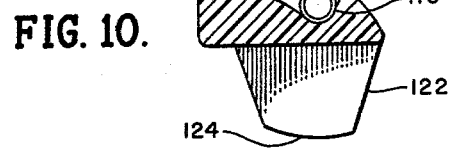
FIG. 9 is a perspective view of a guide block wherein the five walls of the pathway are formed as an integral unit.
FIG. 10 is a cross-sectional view on lines 10—10 showing the pathway profile in broken lines.

FIGS. 9 and 10 show a guide block 100 as an integral unit, preferably made of plastic. The side walls of the pathway 102 are essentially like that of the layout shown in FIG. 5 in the areas that actually do the guiding of the stylus. However, the pathway has been made by machining the opening with a spherical grinding tool so that connecting corner portions 104 between the upper wall 108 and the side walls 110, 112, 114, and 116 are rounded. It is the flat central portions of the walls which guide the stylus rather than those connecting portions.

As seen from FIG. 10, the edges 118 are rounded on a radius rather than formed with the 90 degree edges of the arrangement in FIG. 2. In the area of the rear wall 114 it is helpful that the edge be rounded so that it does not interfere with the shank supporting the spherical stylus that moves in the pathway.

Because the wall surfaces are either flat or curved on a circular radius, the machining of the opening in the guide block is easily automatically programmed and it is practical to produce blocks in that manner. However, it is more practical to use molding techniques using a machined block as a pattern, if a large number of blocks are to be made.

In using an articulator it is often desirable to operate the frames with the styluses locked in the hinge axis position. For this purpose there is provided in each guide block a locking pin 120 extending through the outer side of the block through a bore which opens into the lateral wall 116 of the pathway 102. The bore, and hence the pin 120, is concentrically aligned with the mounting pin 46, which of course has its axis 47 extending through the centric point in the pathway. The pin 120 is axially moveable and can be locked in the selected position by a suitable set screw (not shown). The inner end is formed to smoothly mate with the spherical surface of the stylus 25. With the locking pin 120 engaging the stylus, the articulator frames can only be moved in simple hinging action. With the pin 120 retracted or withdrawn, the stylus can be moved unaffected by the pin.

With the locking pin 120 completely withdrawn, a plate (not shown) having marked thereon a representation of the curve of the upper or superior wall 108 may be temporarily mounted by suitable means on the outer face of the block 100, with the curve aligned with the curve of the wall 108. By rotating the block to align such a curve on the exterior of the block with a curve of a patient's protrusive jaw movement recorded on a transparent sheet (not shown) mounted on a reference surface on the articulator, the block is properly oriented to simulate the jaw movements. This procedure is outlined in greater detail in the above-referenced U.S. Pat. No. 4,034,475.

The block 100 shown in FIGS. 9 and 10 is formed with a leg 122 on its outer side having a curved edge 124. When the block 100 is positioned in an articulator as shown in FIG. 1, the leg 122 extends upwardly beyond the set screw knobs 50. Thus, when the entire articulator is inverted, as is often the case when used, the legs 122 on a set of blocks together with the end of the incisal pin 42 serve as the supporting members. The curved edges 124 on the legs provide a smooth stable surface for the range of rotation that the blocks are rotated.

What is claimed is:

1. In dental apparatus for simulating human jaw movements comprising a first frame having a pair of styluses defining a hinge axis; a second frame having means cooperating with said first frame for guiding movement of said frames relative to each other in a controlled three-dimensional guide path including transverse, protrusive and vertical directions from a centric position wherein the frames are transversely centered on each other and said second frame is in the rearwardmost position relative to said first frame, characterized by:

said guiding means including a pair of guide members each attached to a pin rotatably mounted on said second frame on an axis concentric with said hinge axis when the frames are in said centric position, said guide members having wall means defining pathways for receiving said styluses, said pathways including a curved upper wall, a rear wall and a medial wall having a curved portion adjacent the rear wall, said walls guiding movement of one side of said second frame medially, protrusively and vertically in a curved three-dimensional path while the other side of said second frame moves only laterally;

said wall means defining said pathways further including a forward wall and a lateral wall connected to said medial and said back wall to form an integral side wall unit, separate from but adjacent to said upper wall, which is removeably mounted on said guide members, and which is selected from a group of units that provide different amounts of immediate side shift of said styluses, and said medial wall curved portion being an arc size that is proportional to the magnitude of side shift provided.

2. In dental apparatus for simulating human jaw movements comprising a first frame having a pair of stuluses defining a hinge axis; a second frame having means cooperating with said first frame for guiding movement of said frames relative to each other in a controlled three-dimensional guide path including transverse, protrusive and vertical directions from a centric position wherein the frames are transversely centered on each other and said second frame is in the rearwardmost position relative to said first frame, characterized by:

said guiding means including a pair of guide members each attached to a pin rotatably mounted on said second frame on an axis concentric with said hinge axis when the frames are in said centric position, said guide members having wall means defining pathways for receiving said styluses, said pathways including a curved upper wall, a rear wall and a medial wall having a curved portion adjacent the rear wall, said walls guiding movement of one side of said second frame medially, protrusively and vetically in a curved three-dimensional path while the othr side of said second frame moves only laterally; and said rear wall having a straight central portion and said medial wall having a straight central portion, and said curved portion joins said straight wall portions.

3. The apparatus of claim 2 further characterized by said guide members including a lateral wall having a hole extending through said lateral wall concentric with said mounting pin and having a diameter throughout its length at least as large as said stylus.

4. The articulator of claim 3 further characterized by including a locking pin extending through said hole for locking the stylus in centric position in said pathway, said hole and said locking pin having a diameter equal to said stylus.

* * * * *